United States Patent
Otsuka et al.

(10) Patent No.: US 7,411,086 B2
(45) Date of Patent: Aug. 12, 2008

(54) PROCESS FOR THE PRODUCTION OF N-ALKYLAMINOALKYL (METH)ACRYLATES

(75) Inventors: Shuhei Otsuka, Hiroshima (JP); Akira Ogawa, Hiroshima (JP); Tohru Endoh, Hiroshima (JP); Shingo Tanaka, Hiroshima (JP)

(73) Assignee: Dia-Nitrix Co., Ltd., Tokyo (JP)

( * ) Notice: Subject to any disclaimer, the term of this patent is extended or adjusted under 35 U.S.C. 154(b) by 0 days.

(21) Appl. No.: 10/558,193

(22) PCT Filed: May 27, 2004

(86) PCT No.: PCT/JP2004/007250

§ 371 (c)(1),
(2), (4) Date: Nov. 25, 2005

(87) PCT Pub. No.: WO2004/106278

PCT Pub. Date: Dec. 9, 2004

(65) Prior Publication Data

US 2006/0287550 A1 Dec. 21, 2006

(30) Foreign Application Priority Data

May 28, 2003 (JP) ............................. 2003-150720

(51) Int. Cl.
*C07C 69/52* (2006.01)
(52) U.S. Cl. ...................... 560/205; 560/129
(58) Field of Classification Search ................. 560/205, 560/129
See application file for complete search history.

(56) References Cited

U.S. PATENT DOCUMENTS 6,417,392 B1 * 7/2002 Nagano et al. ............. 560/222

FOREIGN PATENT DOCUMENTS

| DE | 101 27 941 A1 | | 5/2002 |
|---|---|---|---|
| EP | 0 906 902 A2 | | 4/1999 |
| JP | 03-112949 | | 5/1991 |
| JP | 04-095054 | * | 3/1992 |
| JP | 04095054 | | 3/1992 |
| JP | 08-268938 | | 10/1996 |
| JP | 10-279540 | | 10/1998 |
| JP | 11-222469 | | 8/1999 |
| JP | 11-246494 | * | 9/1999 |
| JP | 11-322680 | | 11/1999 |

* cited by examiner

Primary Examiner—Yvonne Eyler
Assistant Examiner—Sudhakar Katakam
(74) Attorney, Agent, or Firm—Oblon, Spivak, McClelland, Maier & Neustadt, P.C.

(57) ABSTRACT

The present invention is to provide a method of producing an N-alkylaminoalkyl (meth)acrylate containing a small amount of low boiling components, especially, containing a small amount of raw components, without any complicated operations or special apparatuses. The method of producing an N-alkylaminoalkyl (meth)acrylate comprising the steps of: (A) performing the reaction between the (meth)acrylic acid ester and the N-alkylaminoalkyl alcohol in a presence of a catalyst to obtain a reaction solution containing the N-alkylaminoalkyl (meth)acrylate; (B) distilling out components which have lower boiling points than the N-alkylaminoalkyl (meth)acrylate from the reaction solution obtained by the step (A); and (C) distilling the N-alkylaminoalkyl (meth)acrylate; and further comprising the step of: (D) adjusting water concentration at a range from 0.01 to 1 wt %. in the reaction solution which is located after the step (A) and before the step (C).

4 Claims, 2 Drawing Sheets

PROCESS FOR THE PRODUCTION OF N-ALKYLAMINOALKYL (METH)ACRYLATES

TECHNICAL FIELD

The present invention relates to a method of producing an N-alkylaminoalkyl(meth)acrylate.

BACKGROUND ART

N-alkylaminoalkyl(meth)acrylates are widely used as raw materials of polymer flocculating agents, lubricating additives, paper strength additives and the like. Above all, when manufacturing a polymer flocculating agent, in some cases, it has to be made to have a high molecular weight to improve its performance, and then there is a problem that a water insoluble gel material is formed. The mechanism of the formation of this gel material has not been fully understood, however, low boiling components contained in an N-alkylaminoalkyl (meth)acrylate, especially (meth)acrylic acid esters and N-alkylaminoalkyl alcohols that are reaction raw materials, are presumed to be a cause of it, and N-alkylaminoalkyl(meth)acrylates containing a small amount of these low boiling components are highly demanded. For example, a concentration of low boiling components contained in an N-alkylaminoalkyl(meth)acrylate is preferably not greater than 0.06 wt %, more preferably not greater than 0.05 wt %, and still more preferably not greater than 0.04 wt %, though it differs depending on a purpose of use and cannot be absolutely said.

Therefore, as a method of producing an N-alkylaminoalkyl (meth)acrylate, the following method is known, wherein an transesterification between a (meth)acrylic acid ester and an N-alkylaminoalkyl alcohol is performed in the presence of a catalyst, then, unreacted raw materials are distilled out from the reaction solution by distillation, and then, distillation of the target product N-alkylaminoalkyl(meth)acrylate is performed. However, there exist by-products of so-called Michael addition reaction (hereinafter referred to as Michael adducts) in the reaction solution formed by an addition reaction of the raw N-alkylaminoalkyl alcohol or a by-product alkyl alcohol to the double bonds of the raw (meth)acrylic acid ester or the target product N-alkylaminoalkyl (meth) acrylate. This Michael addition reaction is a reversible reaction and a decomposing reaction of the Michael adducts takes place not only during the transesterification but also during the following stages of distilling out the raw materials and distilling the target product, therefore, there is a problem that low boiling components such as the raw materials mix with the target product N-alkylaminoalkyl(meth)acrylate. To cope with this problem, various measures have been taken.

As a method of producing an N-alkylaminoalkyl(meth) acrylate containing a small amount of low boiling components, Patent document 1 and Patent document 2 disclose a method of producing a high purity N-alkylaminoalkyl(meth) acrylate, separating a catalyst from a reaction solution in advance to distilling out the low boiling components and refining a target product in a stage of refining after performing an transesterification in a presence of a catalyst.

Further, Patent document 3 and Patent document 4 disclose a method of reducing low boiling components in an N-alkylaminoalkyl(meth)acrylate by pyrolysis treatment of by-products.

In addition, Patent document 5 discloses a method of suppressing side reactions by adding the raw N-alkylaminoalkyl alcohol to the reaction system with a passage of time.

Patent document 1: Japanese Patent Application Laid-Open No. 11-322680.

Patent document 2: Japanese Patent Application Laid-Open No. 3-112949.

Patent document 3: Japanese Patent Application Laid-Open No. 11-222469.

Patent document 4: Japanese Patent Application Laid-Open No. 10-279540.

Patent document 5: Japanese Patent Application Laid-Open No. 4-95054.

Patent document 6: Japanese Patent Application Laid-Open No. 8-268938.

DISCLOSURE OF INVENTION

According to the methods disclosed in Patent document 1 and Patent document 2, an additional step for separating the catalyst and the N-alkylaminoalkyl(meth)acrylate from the reaction solution is necessary, causing a problem of cost increase.

Also, according to the methods disclosed in Patent document 3 and Patent document 4, an additional apparatus for the pyrolysis treatment of the by-products is necessary, causing a problem of cost increase, and further considerable time is necessary for this pyrolysis, causing a problem of productivity decrease.

According to the method disclosed in Patent document 5, the N-alkylaminoalkyl(meth)acrylate contains around 2000 ppm (0.2 wt %) of impurities and it is difficult to refine it sufficiently.

The present invention has been achieved taking into consideration of the above-mentioned problems and the objective of the present invention is to provide a method of producing an N-alkylaminoalkyl(meth)acrylate containing a small amount of low boiling components, especially, containing a small amount of raw components, without any complicated operations or special apparatuses.

The above-mentioned objective can be achieved by the present invention mentioned below.

Namely, the present invention is a method of producing an N-alkylaminoalkyl(meth)acrylate by a reaction between a (meth)acrylic acid ester and an N-alkylaminoalkyl alcohol, comprising the steps of:

(A) performing the reaction between the (meth)acrylic acid ester and the N-alkylaminoalkyl alcohol in a presence of a catalyst to obtain a reaction solution containing the N-alkylaminoalkyl(meth)acrylate;

(B) distilling out components which have lower boiling points than the N-alkylaminoalkyl(meth)acrylate from the reaction solution obtained by the step (A); and (C) distilling the N-alkylaminoalkyl(meth)acrylate;

and further comprising the step of:

(D) adjusting water concentration at a range from 0.01 to 1 wt % in the reaction solution which is located after the step (A) and before the step (C).

According to the method of producing an N-alkylaminoalkyl (meth)acrylate disclosed in the present invention, N-alkylaminoalkyl (meth)acrylates containing a small amount of low boiling components, especially, containing a small amount of raw components can be obtained without any complicated operations or special apparatuses.

In the method of producing an N-alkylaminoalkyl(meth) acrylate disclosed in the present invention, the (meth)acrylic acid ester is preferable to be a compound represented by the following formula (1):

wherein $R^1$ denotes hydrogen or methyl group and $R^2$ denotes an alkyl group containing 1 to 2 carbon atoms. Further, in the step (D), it is preferable to introduce water into the reaction solution which is located after the step (A) and before the step (C). Moreover, it is preferable that the step (D) is performed before the step (B).

It is possible to reuse at least a part of the catalyst contained in a residue remaining after the step (C) of the method of producing an N-alkylaminoalkyl (meth)acrylate for a reaction between a (meth)acrylic acid ester and an N-alkylaminoalkyl alcohol.

In the present invention, a term "(meth)acrylic acid" means methacrylic acid or acrylic acid.

According to the present invention, it is possible to obtain N-alkylaminoalkyl(meth)acrylates containing a small amount of low boiling components, especially, containing a small amount of raw components without any complicated operations or special apparatuses.

EXPLANATION OF THE SIGN

Figure 1:
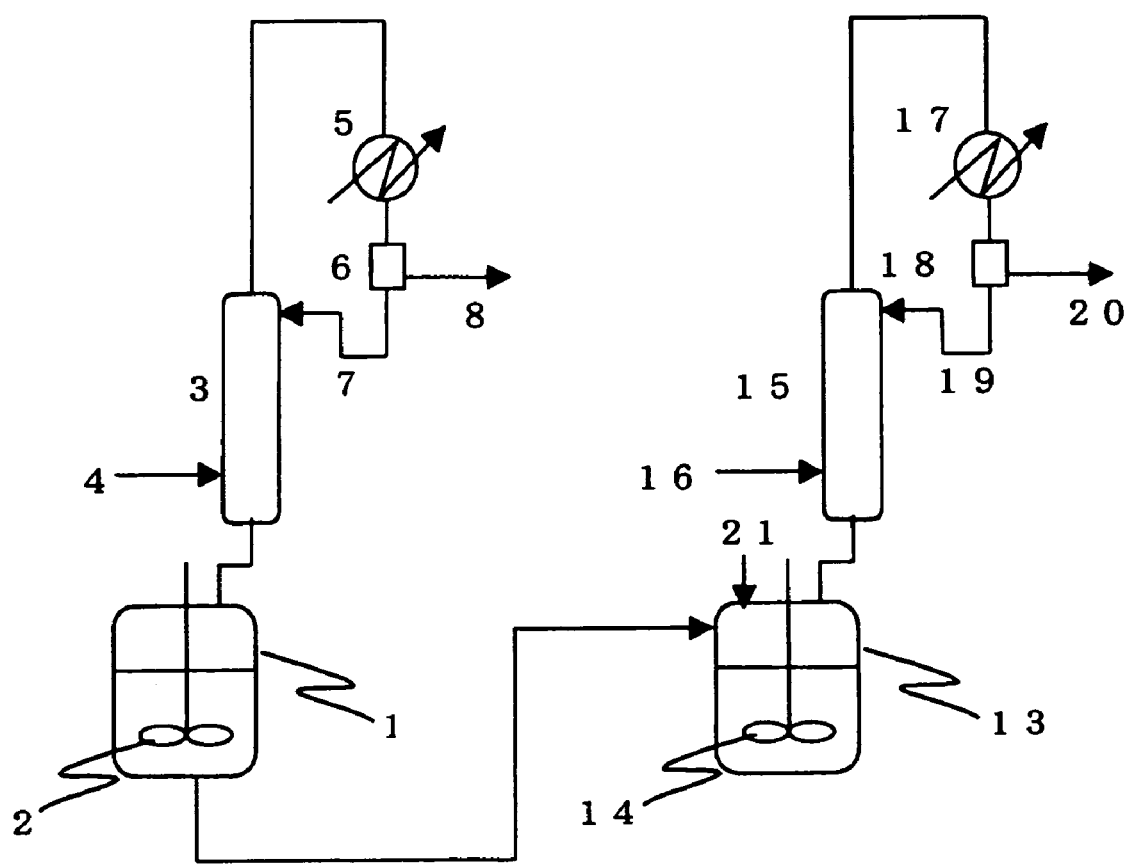
FIG. 1 is a diagram showing an example of a manufacturing apparatus which can be used for a method of producing an N-alkylaminoalkyl (meth)acrylate in the present invention.

1: distillation still
2: stirrer
3: distillation column
4: gas introduction port
5: condenser
6: liquid distributor
7: reflux line
8: distilling out line
9: water supply line
10: decanter
11: upper layer reflux line
12: lower layer drawing out line
13: distillation still
14: stirrer
15: distillation column
16: gas introduction port
17: condenser
18: liquid distributor
19: reflux line
20: distilling out line
21: water supply port

BEST MODE FOR CARRING OUT THE INVENTION

The method of producing an N-alkylaminoalkyl(meth) acrylate disclosed in the present invention has the step (A):

(A) performing the reaction between the (meth)acrylic acid ester and the N-alkylaminoalkyl alcohol in a presence of a catalyst to obtain a reaction solution containing the N-alkylaminoalkyl(meth)acrylate.

In the present invention, methyl(meth)acrylate, ethyl (meth)acrylate, isopropyl(meth)acrylate, n-butyl(meth)acrylate and the like can be used as the raw (meth)acrylic acid ester. Among them, because of easiness of performing the transesterification reaction, compounds represented by the following formula (1), that are methyl(meth)acrylate and ethyl(meth)acrylate, are preferable:

wherein $R^1$ denotes hydrogen or methyl group and $R^2$ denotes an alkyl group containing 1 to 2 carbon atoms. Particularly, methyl(meth)acrylate is preferable.

In the present invention, an appropriate N-alkylaminoalkyl alcohol corresponding to the target product N-alkylaminoalkyl(meth)acrylate, for example, 2-dimethylaminoethanol, 2-diethylaminoethanol and the like, can be used as the raw N-alkylaminoalkyl alcohol.

In the present invention, a ratio of the (meth)acrylic acid ester to the N-alkylaminoalkyl alcohol can be set up optionally, but from the viewpoint of productivity, the ratio of the (meth)acrylic acid ester to 1 mol of the N-alkylaminoalkyl alcohol is usually 0.1 to 10 mol, and more preferably 0.5 to 4 mol. In addition, the raw (meth)acrylic acid ester and/or the raw N-alkylaminoalkyl alcohol may be properly added to the reaction system during the transesterification.

As a catalyst used in the present invention, well known catalysts for transesterification may be used and examples of the catalyst include metal alcoholate catalyst such as alkali metal alcoholate, magnesium alcoholate, titanium alcoholate and the like and tin containing catalyst such as dibutyltin oxide, dioctyltin oxide and the like. In the present invention, especially tin containing catalyst is preferable from the viewpoint of the reaction activity and selectivity to the target product. An amount of the catalyst to be used is usually 0.0001 to 0.1 mol per 1 mol of N-alkylaminoalkyl alcohol.

In the above-mentioned transesterification, the pressure is not particularly limited and normal pressure, reduced pressure or increased pressure can be chosen. The reaction temperature can be usually selected from 60° C. to 150° C.

Since the above-mentioned transesterification is an equilibrium reaction, it is desirable to carry out the reaction while removing a by-product alkyl alcohol. Solvents are not always necessary in the above-mentioned transesterification, however, it is possible to use a solvent in order to remove the by-product alkyl alcohol as an azeotrope. The examples of the solvent to be used include n-pentane, n-hexane, n-heptane, benzene, toluene, cyclohexane and so forth. When using a solvent, the following method disclosed in Patent document 6 can be applied.

Namely, it can be applied that the by-product alkyl alcohol is distilled out together with an azeotropic solvent as an azeotrope by a distillation operation, then a portion of the mixture is refluxed to a top stage of distillation column, and the remainder is mixed with water and separated into two layers by a decanter, then the upper layer which is mainly composed of the azeotropic solvent is refluxed to the column, and the lower layer which is mainly composed of water and the alkyl alcohol is removed from the system.

When performing an transesterification such as the one mentioned above, a polymerization inhibitor is usually added into a reaction solution to inhibit the polymerization of the raw (meth)acrylic acid ester or the reaction product N-alkylaminoalkyl(meth)acrylate. The polymerization inhibitor to be used is not particularly limited and ones well known can be used, which include hydroquinone, hydroquinone-monomethylether, phenothiazine, N,N'-di-2-naphthyl-p-phenylenediamine, N-oxyl compounds and so on. An amount of the polymerization inhibitor to be added is preferably 0.001 to 2 wt % to the weight of the reaction solution.

Further, it is preferable to supply oxygen or a mixture of oxygen and inert gas such as air, mixed gas of oxygen and argon and the like to the reaction system of transesterification, because the effect of inhibition on the polymerization of the raw (meth)acrylic acid ester or the reaction product N-alkylaminoalkyl(meth)acrylate is further enhanced.

When conducting the transesterification, it is desirable to use a distillation apparatus. The distillation apparatus to be used is not particularly limited and the ones well known can be used, which include tray-type distillation column, packed column type distillation column, wiped film evaporator, and so on.

A type of the reaction can be the one generally used, and examples of which include batch type, continuous type and so on.

In order to remove the by-product alkyl alcohol from the system, azeotropy of an azeotropic solvent or (meth)acrylic acid ester and the by-product alkyl alcohol can be used. To suppress a loss of raw (meth)acrylic acid ester caused by its excessive distilling out, it is preferable to control the temperature of the top stage of distillation column to be kept at an azeotropic temperature, and accordingly, it is preferable that the reflux composition is to be an azeotropic composition. However, mutual solubility in an azeotrope, in general, is low and it is occasionally happen that a condensate in a condenser separates into two layers of which the upper layer is composed mainly of the azeotropic solvent and the lower layer is composed mainly of the by-product alkyl alcohol. In case the condensate has two separated layers, a reflux composition inclines toward upper layer composition or lower layer composition and shifts from an azeotropic composition, and accordingly, it is preferable to reflux the condensate after adjusting it to the azeotropic composition. The method of making a condensate composition come near to an azeotropic composition may be one using static mixer or pump and giving the condensate a mechanical energy to make it come near to an azeotropic composition and one using decanter and separating the condensate into two layers and adjusting both upper and lower layers to become the azeotropic composition and refluxing them.

In a reaction solution after conducting such an transesterification, a reaction product N-alkylaminoalkyl(meth)acrylate and a catalyst are included and, in addition, in many cases, low boiling components such as raw materials may be included. Further, by-product Michael adducts by a side reaction, Michael addition reaction, are usually included, and moreover, decomposed components of the Michael adducts may exist in the reaction solution obtained in the step (A), because the Michael addition reaction is a reversible reaction.

Therefore, in the present invention, there are steps (B) and (C) after the above-mentioned reaction:

(B) distilling out components which have lower boiling points than the N-alkylaminoalkyl(meth)acrylate from the reaction solution obtained by the step (A);

(C) distilling the N-alkylaminoalkyl(meth)acrylate.

When conducting the steps (B) and (C), it is desirable to use a distillation apparatus. The distillation apparatus to be used is not particularly limited and the ones well known can be used, which include tray-type distillation column, packed column type distillation column, wiped film evaporator, and so on. The distillation apparatus used in the step (A) or other distillation apparatus may be used. A type of the reaction can be the one generally used, and examples of which include batch type, continuous type and so on.

As conditions of the steps (B) and (C), it may be chosen appropriately to be able to obtain as pure N-alkylaminoalkyl (meth)acrylate as possible in the step (C). Usually, components contained in a reaction solution obtained in the step (A) and having lower boiling points than the N-alkylaminoalkyl (meth)acrylate are mostly raw materials, therefore, it is preferable to choose a condition in such a way that, in the step (B), the raw materials can be distilled out and recovered, and, in the step (C), the N-alkylaminoalkyl(meth)acrylate can be distilled. The pressure is not particularly limited and normal pressure, reduced pressure or increased pressure can be chosen, however, because the raw (meth)acrylic acid ester and the reaction product N-alkylaminoalkyl (meth)acrylate are liable to polymerize by heat, it is preferable to choose reduced pressure which makes it possible to recover them at a low temperature.

Further, when conducting the steps (B) and (C), it is desirable to add a polymerization inhibitor or to supply oxygen or a mixture of oxygen and inert gas into a reaction solution of the steps (B) and (C), as well as in the step (A), to inhibit the polymerization of the remaining raw (meth)acrylic acid ester and the N-alkylaminoalkyl(meth)acrylate. In case the same apparatus is used in the steps (B) and (C) as in the step (A), the polymerization inhibitor used in the step (A) can inhibit polymerization in the steps (B) and (C), so that it is not necessary to add a polymerization inhibitor again to these steps.

Furthermore, in the present invention, there is the following step (D):

(D) adjusting water concentration at a range from 0.01 to 1 wt % in the reaction solution which is located after the step (A) and before the step (C).

By performing the step (D), low boiling components, especially raw components, can be considerably reduced in the resulting N-alkylaminoalkyl (meth)acrylate. Although the mechanism of this phenomenon is not fully elucidated, it is thought that the decomposition reaction of the Michael adducts is suppressed with the water.

Then, it is important to adjust the water concentration at a range from 0.01 to 1 wt %. By making the water concentration not less than 0.01 wt %, it is possible to adequately reduce low boiling components. Further, by making the water concentration not greater than 1 wt %, it is possible to reuse the catalyst contained in the residue remaining after the step (C) for the transesterification, though it depends on the kind of a catalyst. The water concentration is preferably 0.015 to 0.5 wt %, and more preferably 0.015 to 0.2 wt %. And, in the present invention, water concentration is measured with Karl Fischer method.

In the step (D), as the method of adjusting water concentration in the reaction solution which is located after the step (A) and before the step (C), the followings can be chosen:

(i) introducing water into the reaction solution;

(ii) placing the reaction solution under humidity controlled atmosphere;

(iii) introducing water vapor into the reaction solution;

(iv) adjusting a water removing condition in the transesterification; and so on, and it is preferable to choose (i) introducing water into a reaction solution because of easiness of adjusting the concentration.

Moreover, it is important to carry out the adjustment of the water concentration in the step (D) in the reaction solution which is located after the step (A) and before the step (C). In other words, it is important to make the water concentration in the reaction solution after the step (A) and before the step (C) pass the state of 0.01 to 1 wt %. It is preferable to carry out the step (D) before the step (B), because water can be removed as a low boiling component in the step (B). The adjustment of the water concentration in the step (D) can be carried out plural times with the reaction solution after the step (A) and before the step (C). Further it can be carried out continuously with the reaction solution after the step (A) and before the step (C). In addition, it is desirable to carry out the step (D) under the condition that the temperature of the reaction solution is not higher than 90° C.

Figure 2:
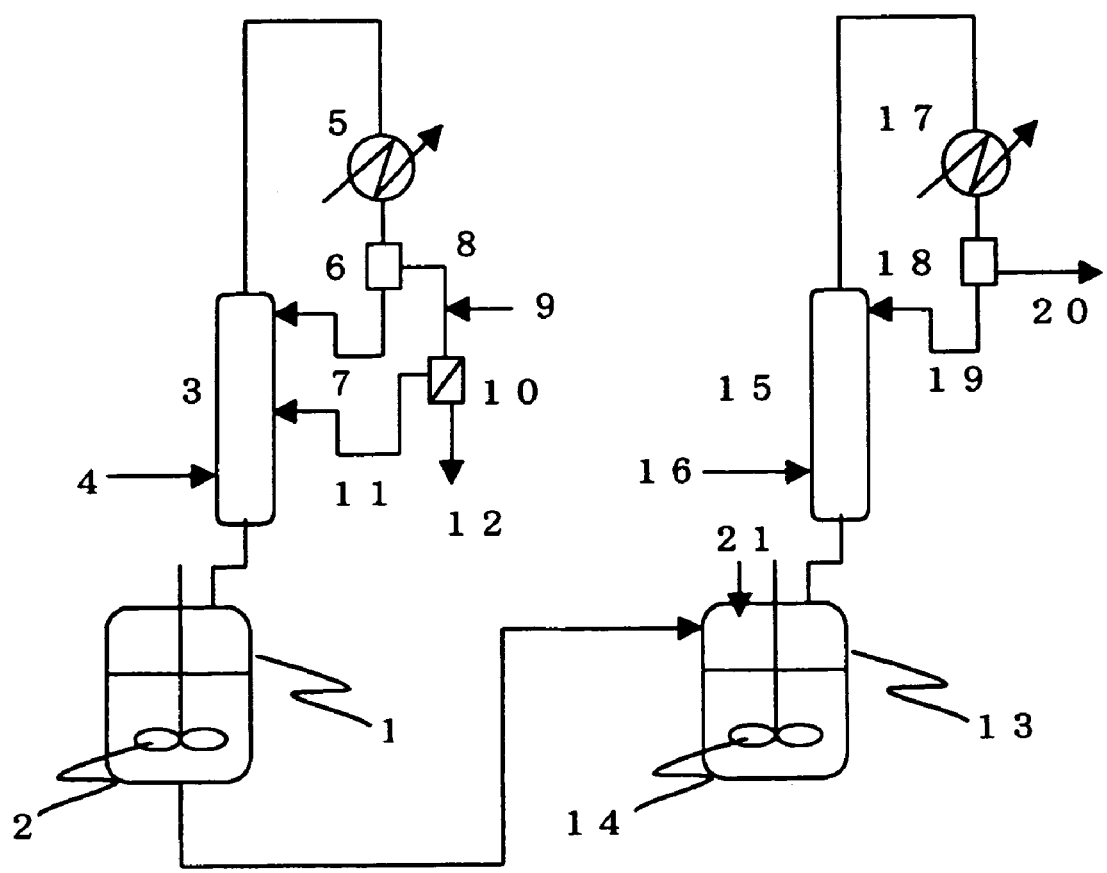
FIG. 2 is a diagram showing an example of a manufacturing apparatus which can be used for a method of producing an N-alkylaminoalkyl (meth)acrylate in the present invention.

FIG. 1 and FIG. 2 are diagrams showing examples of manufacturing apparatuses which can be used for a method of producing an N-alkylaminoalkyl (meth)acrylate in the present invention. Hereinafter, the producing method using these apparatuses is explained as a mode of enforcement.

In a distillation still 1 equipped with a stirrer 2, an transesterification between a raw (meth)acrylic acid and an N-alkylaminoalkyl alcohol in a presence of a catalyst is carried out. A by-product alkyl alcohol and its azeotrope are passed through a distillation column 3 and condensed at a condenser 5, and by way of a liquid distributor 6, a portion of the condensate is refluxed to the top stage of distillation column through a reflux line 7. The remainder of the condensate is drawn out through a distilling out line 8 in the case of the apparatus shown FIG. 1. On the other hand, when using a solvent which has low compatibility with water as an azeotropic solvent, the apparatus shown in FIG. 2 can be suitably used. In the case of the apparatus in FIG. 2, the remainder of the condensate is mixed at the distilling out line 8 with water from a water supply line 9, and introduced into a decanter 10. At the decanter 10, the upper layer can be refluxed to the distillation column 3 by way of an upper layer reflux line 11, and the lower layer can be drawn out from a lower layer drawing out line 12. To the reaction system, oxygen contained gas for the purpose of polymerization inhibition can be introduced through a gas introduction port 4.

After finishing transesterification, the reaction solution containing an N-alkylaminoalkyl(meth)acrylate is transferred into another distillation still 13 equipped with a stirrer 14, then, the unreacted raw (meth)acrylic acid ester and N-alkylaminoalkyl alcohol are distilled out from the top of a distillation column 15, and further, the target product N-alkylaminoalkyl(meth)acrylate is distilled. A vapor distilled from the top stage of distillation column is condensed in a condenser 17, and by way of a liquid distributor 18, a portion of the condensate can be refluxed to the top stage of distillation column through a reflux line 19, as well as recovered through a distilling out line 20. An oxygen contained gas for the purpose of polymerization inhibition can be introduced through a gas introduction port 16. Further, it is possible to make water co-exist with the reaction solution by introducing water from a water supply port 21. According to the method of the present invention, it is preferable to make water co-exist with the reaction solution which is located after the transesterification and before the distillation of the N-alkylaminoalkyl(meth)acrylate as mentioned before.

A catalyst used in a method of producing an N-alkylaminoalkyl (meth)acrylate of the present invention is included in a residue remaining after the step (C), at least a part of which can be reused in an transesterification between a (meth)acrylic acid ester and an N-alkylaminoalkyl alcohol. Either entire amount or a part of the residue may be used. Further, it is no problem to add a fresh catalyst when reusing it.

In addition, when reusing the catalyst as mentioned above, it is preferable to take the method mixing at least a part of raw materials of a transesterification in which the catalyst is reused with a residue remaining after the step (C), and recovering the catalyst as a mixed solution, because the handling of the catalyst become easy. As a raw material to be mixed, either (meth)acrylic acid ester or N-alkylaminoalkyl alcohol may be used, and particularly, (meth)acrylic acid ester is more preferable. However, it is important that the raw material to be mixed should be a raw material of an transesterification in which the catalyst is reused. It is not always necessary that the raw material to be mixed should be the one used in the preceding transesterification but it is preferable that the raw material is reused in the same transesterification using the same raw materials, because a purer product can be obtained.

EXAMPLES

Hereinafter, the present invention will be described in detail with reference to the following examples.

Example 1

688 g of 2-dimethylamino ethanol, 1242 g of methyl acrylate, 28 g of dibutyltin oxide as a catalyst and 2 g of phenothiazine as a polymerization inhibitor were charged in a 3 liter still equipped with a stirrer, a thermometer, a 20 stages Oldershaw type distillation column, a cooling equipment, a liquid distributor and a decanter, and a reaction was carried out under atmospheric pressure. Further, 300 g of n-hexane was introduced as an azeotropic solvent. To this reaction apparatus, nitrogen/oxygen mixed gas with an oxygen concentration of 8% was introduced at 10 ml/min for polymerization inhibition. The reaction temperature changed from 85° C. to 100° C. in the course of the reaction. By-product methanol was distilled out from the top stage of distillation column together with n-hexane as an azeotropic mixture, and a portion of the condensate was refluxed to the top stage of distillation column so as to make the temperature of the fifth stage from the top stage of distillation column become 50° C., and the remainder was mixed with water which was supplied at 137 g/h and introduced into the decanter. Further, the condensate introduced in to the decanter was separated into two layers, and the upper layer was refluxed to the fifteenth stage from the top stage of distillation column, and the lower layer was drawn out so that the interlayer of the decanter was kept to a constant level. The temperature of the top stage of distillation column was kept at 50° C. throughout the reaction.

After 6 hours from the start of the reaction, when the conversion of 2-dimethylamino ethanol reached 95%, a total distilling out operation was carried out in order to distill methanol in the distillation column out from the system. The conversion was defined as in the following formula, wherein $M_a$ represents a mole number of raw 2-dimethylamino ethanol and Mb represents a mole number of target product 2-dimethylaminoethyl acrylate, and practically calculated from a mass ratio obtained by gas chromatography (detector: FID) and a molecular weight.

$$\text{Conversion (\%)} = [M_b/(M_a+M_b)] \times 100$$

Then, to 2007 g of the reaction solution thus obtained (water concentration was 0.0066 wt %), 2 g of water (equivalent to 0.1 wt %) was added, and distilling out of low boiling components and distillation of the target product 2-dimethylaminoethyl acrylate was carried out.

The reaction solution was introduced into a 3 liter still equipped with a stirrer, a thermometer, a 20 stages Oldershaw type distillation column, a cooling equipment, a liquid distributor and a vacuum pump, and the pressure of the system was gradually reduced to 1.3 kPa by taking 3.5 hours, and unreacted methyl acrylate and 2-dimethylamino ethanol were distilled out from the top stage of distillation column. The final temperature of the distillation still and the top stage of distillation column were 87° C. and 65° C., respectively. Then, 2-dimethylaminoethyl acrylate was distilled out under the reduced pressure of 1.3 kPa for 1 hour. At that time, the temperature of the distillation still and the top stage of distillation column were 87° C. and 65° C., respectively.

The mass of 2-dimethylaminoethyl acrylate thus obtained was 693 g, wherein 0.0122 wt % of methyl acrylate and 0.0134 wt % of 2-dimethylamino ethanol, that is 0.0256 wt % of the total, were contained, therefore, 2-dimethylaminoethyl acrylate with a small amount of raw components could be obtained. The concentrations of the raw components were obtained by gas chromatography (detector: TCD).

Example 2

A procedure was carried out in the same manner as in Example 1, except that the amount of water added after the transesterification was 1 g (equivalent to 0.05 wt %).

The mass of 2-dimethylaminoethyl acrylate thus obtained was 685 g, wherein 0.0128 wt % of methyl acrylate and 0.0185 wt % of 2-dimethylamino ethanol, that is 0.0313 wt % of the total, were contained, therefore, 2-dimethylaminoethyl acrylate with a small amount of raw components could be obtained.

Further, using 109 g of the residue remained in the distillation still instead of a catalyst, the transesterification was carried out in the same manner as in Example 1. After 6 hours from the start of the reaction, the conversion of 2-dimethylamino ethanol reached 95%, and therefore, the reactivity of the catalyst was the same.

To the reaction solution thus obtained (water concentration was 0.0055 wt %), 1 g of water (equivalent to 0.05 wt %) was added and the same procedure as in Example 1 was carried out.

The mass of 2-dimethylaminoethyl acrylate thus obtained was 716 g, wherein 0.0101 wt % of methyl acrylate and 0.0146 wt % of 2-dimethylamino ethanol, that is 0.0247 wt % of the total, were contained, therefore, 2-dimethylaminoethyl acrylate with a small amount of raw components could be obtained.

Comparative Example 1

A procedure was carried out in the same manner as in Example 1, except that water was not added. Then, the water concentration in the reaction solution after the transesterification was 0.0070 wt %.

The mass of 2-dimethylaminoethyl acrylate thus obtained was 680 g, wherein 0.0557 wt % of methyl acrylate and 0.0425 wt % of 2-dimethylamino ethanol, that is 0.0982 wt % of the total were contained.

INDUSTRIAL APPLICABILITY

The method of the present invention is suitable for producing N-alkylaminoalkyl(meth)acrylates which can be used as raw materials of polymer flocculating agents, lubricating additives, paper strength additives and the like, and the products with low price and high purity can be obtained.

What is claimed is:

1. A method of producing an N-alkylaminoalkyl (meth) acrylate by a reaction between a (meth)acrylic acid ester and an N-alkylaminoalkyl alcohol, comprising:
    (A) performing the reaction between the (meth)acrylic acid ester and the N-alkylaminoalkyl alcohol in a presence of a catalyst to obtain a reaction solution containing the N-alkylaminoalkyl (meth)acrylate;
    (B) distilling out components which have lower boiling points than the N-alkylaminoalkyl (meth)acrylate from the reaction solution obtained by the step (A); and
    (C) distilling the N-alkylaminoalkyl (meth)acrylate;
    and further comprising:
    (D) adjusting a water concentration at a range from 0.01 to 1 wt % in the reaction solution by introducing water into the reaction solution which is located after the step (A) and before the step (B).

2. The method of producing an N-alkylaminoalkyl (meth) acrylate according to claim 1, wherein the (meth)acrylic acid ester is a compound represented by the following formula (1):

$$CH_2=CR^1COOR^2 \qquad (1)$$

wherein $R^1$ denotes hydrogen or methyl group and $R^2$ denotes an alkyl group containing 1 to 2 carbon atoms.

3. A method of producing an N-alkylaminoalkyl (meth) acrylate, reusing at least a part of the catalyst contained in a residue remaining after the step (C) of the method of producing an N-alkylaminoalkyl (meth)acrylate according to claim 1 for a reaction between a (meth)acrylic acid ester and an N-alkylaminoalkyl alcohol.

4. A method of producing an N-alkylaminoalkyl (meth) acrylate, reusing at least a part of the catalyst contained in a residue remaining after the step (C) of the method of producing an N-alkylaminoalkyl (meth)acrylate according to claim 2 for a reaction between a (meth)acrylic acid ester and an N-alkylaminoalkyl alcohol.

* * * * *